United States Patent
Yokoi et al.

(10) Patent No.: US 8,147,771 B2
(45) Date of Patent: Apr. 3, 2012

(54) STERILIZING MATERIAL SUPPLY APPARATUS AND ISOLATOR

(75) Inventors: Yasuhiko Yokoi, Ota (JP); Jiro Ohnishi, Ota (JP); Akifumi Iwama, Tsukuba (JP); Masaki Harada, Yawata (JP); Yoshiaki Noguchi, Ota (JP)

(73) Assignee: Sanyo Electric Co., Ltd., Osaka (JP)

( * ) Notice: Subject to any disclaimer, the term of this patent is extended or adjusted under 35 U.S.C. 154(b) by 241 days.

(21) Appl. No.: 12/697,702

(22) Filed: Feb. 1, 2010

(65) Prior Publication Data
US 2010/0196216 A1 Aug. 5, 2010

(30) Foreign Application Priority Data

Jan. 30, 2009 (JP) .................................. 2009-020984
Dec. 25, 2009 (JP) .................................. 2009-293676

(51) Int. Cl.
*A61L 9/00* (2006.01)
*B01J 7/00* (2006.01)
(52) U.S. Cl. .................... 422/305; 422/123; 422/306
(58) Field of Classification Search .................. 422/123, 422/305, 306, 28, 29
See application file for complete search history.

(56) References Cited

U.S. PATENT DOCUMENTS

| 5,173,258 A | 12/1992 | Childers |
| 6,746,652 B2 * | 6/2004 | Khorzad et al. .............. 422/305 |

FOREIGN PATENT DOCUMENTS

| JP | 2005-312799 | 11/2005 |
| JP | 2006-068122 | 3/2006 |
| JP | 2006-320392 | 11/2006 |
| WO | WO 2005/036151 A2 | 4/2005 |
| WO | WO 2008/116341 A2 | 10/2008 |

OTHER PUBLICATIONS

European Search Report issued in European Patent Application No. EP 10000769.9 dated Apr. 14, 2010.

* cited by examiner

*Primary Examiner* — Sean E Conley
(74) *Attorney, Agent, or Firm* — McDermott Will & Emery LLP

(57) ABSTRACT

A sterilizing material supply apparatus has a sterilizing material gas generator including a mist generation unit and a vaporizing unit. In the mist generation unit, hydrogen peroxide solution in a cup is converted into a mist by ultrasonic vibration generated by an ultrasonic vibrator. The hydrogen peroxide solution which has been turned into the mist is heated by a heater in the vaporizing unit so as to be gasified. The gasified hydrogen peroxide solution is supplied to a workroom of an isolator as a sterilizing gas.

5 Claims, 5 Drawing Sheets

STERILIZING MATERIAL SUPPLY APPARATUS AND ISOLATOR

CROSS-REFERENCE TO RELATED APPLICATIONS

This application is based upon and claims the benefit of priority from the prior Japanese Patent Applications No. 2009-20984, filed on Jan. 30, 2009, and Japanese Patent Applications No. 2009-293676, filed on Dec. 25, 2009, the entire contents of which are incorporated herein by reference.

BACKGROUND OF THE INVENTION

1. Field of the Invention

The present invention relates to a bio isolator, for example, and a sterilizing material supply apparatus for use in the isolator.

2. Description of the Related Art

A bio isolator, an isolator for bio research, a biohazard isolator or the like is a system having a sterilized workroom, in which operations that require a sterile environment, such as those involving biologically-derived materials obtained by cell culture, for instance, are performed. The sterile environment meant here is an environment substantially free of dust and germs such that it allows no entry of substances other than the materials used in the work done in the workroom.

The workroom is equipped with a gas supply port and a gas discharge port. Air outside the isolator is supplied into the workroom through the gas supply port, and the air in the workroom is discharged through a gas discharge port. Generally, the isolator is provided with a particulate trap filter, such as a HEPA (High-Efficiency Particulate Air) filter, at the gas supply port in order to keep a sterile environment for the workroom, and the outside air is supplied into the workroom through the particulate trap filter. Also, a particulate trap filter is provided at the gas discharge port, and the air inside the workroom is discharged outside through the particulate trap filter.

Also, in the isolator, a sterilization treatment is conducted in the workroom with a sterilizing material (sterilizing agent), such as hydrogen peroxide gas, sprayed into them.

In the sterilization treatment, a gaseous sterilizing material is supplied into the workroom. In a conventional isolator, when a sterilizing material is sterilized, a long time duration is required until the sterilizing material is turned into a gas. Thus, the overall sterilization process takes a long time, causing a problem of reduced work efficiency in the isolator.

SUMMARY OF THE INVENTION

The present invention has been made to solve such problems, and a purpose thereof is to provide a technology by which to reduce the time required for a sterilization treatment and enhance the work efficiency in an isolator.

One embodiment of the present invention relates to a sterilizing material supply apparatus. The sterilizing material supply unit comprises: (1) a mist generation unit including: a propagation fluid holding unit for holding a fluid through which ultrasonic vibration generated by an ultrasonic vibrator attached to a bottom of the holding unit propagates; and a receptacle for holding a hydrogen peroxide solution which is a raw material for sterilizing material, the receptacle being attached to the propagation fluid holding unit in such a manner as to cover an upper opening of the propagation fluid holding unit, and a bottom of the receptacle projecting toward the ultrasonic vibrator; and (2) a vaporizing unit configured to heat and vaporize the hydrogen peroxide solution atomized by the mist generation unit, the vaporizing unit including: a carrier gas supply port installed upright above the mist generation unit, wherein a lower opening of the carrier gas supply port communicates with the receptacle and a carrier gas carrying the hydrogen peroxide solution atomized thereby flows into a lower side face of the carrier gas supply port; a heating pipe, disposed on top thereof, having a hydrogen peroxide supply port for supplying hydrogen peroxide, together with the carrier gas, to the exterior; and a heater disposed inside the heating pipe, wherein the hydrogen peroxide solution atomized by the mist generation unit is fed to the vaporizing unit using the carrier gas, and a hydrogen peroxide gas, vaporized by the vaporizing unit, together with the carrier gas is supplied to the exterior.

By employing the sterilizing material supply apparatus according to the above-described embodiment, a two-stage method is implemented where the hydrogen peroxide is atomized (i.e., the generation of mists) by the mist generation unit having the ultrasonic vibrator followed by the vaporization (gasification) thereof by the vaporizing unit. As a result, the gasification of hydrogen peroxide can be conducted promptly. Also, the quantity of heat used in the vaporizing unit can be reduced as compared with the conventional practice. Thus, the time duration required for the gasification of hydrogen peroxide can be shortened and consequently the process of sterilization as a whole can be shortened. As a result, the work efficiency in the isolator can be improved.

Another embodiment of the present invention relates to an isolator. The isolator has a workroom in which a work involving biologically-derived materials is performed, and the isolator comprises: (1) a mist generation unit including: (i) a propagation fluid holding unit for holding a fluid through which ultrasonic vibration generated by an ultrasonic vibrator attached to a bottom of the holding unit propagates; and a (ii) receptacle for holding a hydrogen peroxide solution which is a raw material for sterilizing material, the receptacle being attached onto the propagation fluid holding unit in such a manner as to cover an upper opening of the propagation fluid holding unit, and a bottom of the receptacle projecting toward the ultrasonic vibrator; and (2) a vaporizing unit configured to heat and vaporize the hydrogen peroxide solution atomized by the mist generation unit, wherein the vaporizing unit is installed upright above said mist generation unit and a lower opening thereof communicates with the receptacle, the vaporizing unit including: (i) a carrier gas supply port into which a carrier gas carrying the hydrogen peroxide solution atomized thereby flows through a lower side face of said vaporizing unit; (ii) a heating pipe, disposed on top thereof, having a hydrogen peroxide supply port for supplying hydrogen peroxide, together with the carrier gas, to the exterior; and (iii) a heater disposed inside the heating pipe, wherein the hydrogen peroxide solution atomized by the mist generation unit is fed to the vaporizing unit using the carrier gas, and a hydrogen peroxide gas, vaporized by the vaporizing unit, together with the carrier gas is supplied to the exterior.

It is to be noted that any arbitrary combinations or rearrangement, as appropriate, of the aforementioned constituting elements and so forth are all effective as and encompassed by the embodiments of the present invention.

BRIEF DESCRIPTION OF THE DRAWINGS

Embodiments will now be described by way of examples only, with reference to the accompanying drawings which are meant to be exemplary, not limiting and wherein like elements are numbered alike in several Figures in which.

DETAILED DESCRIPTION OF THE INVENTION

Figure 1:
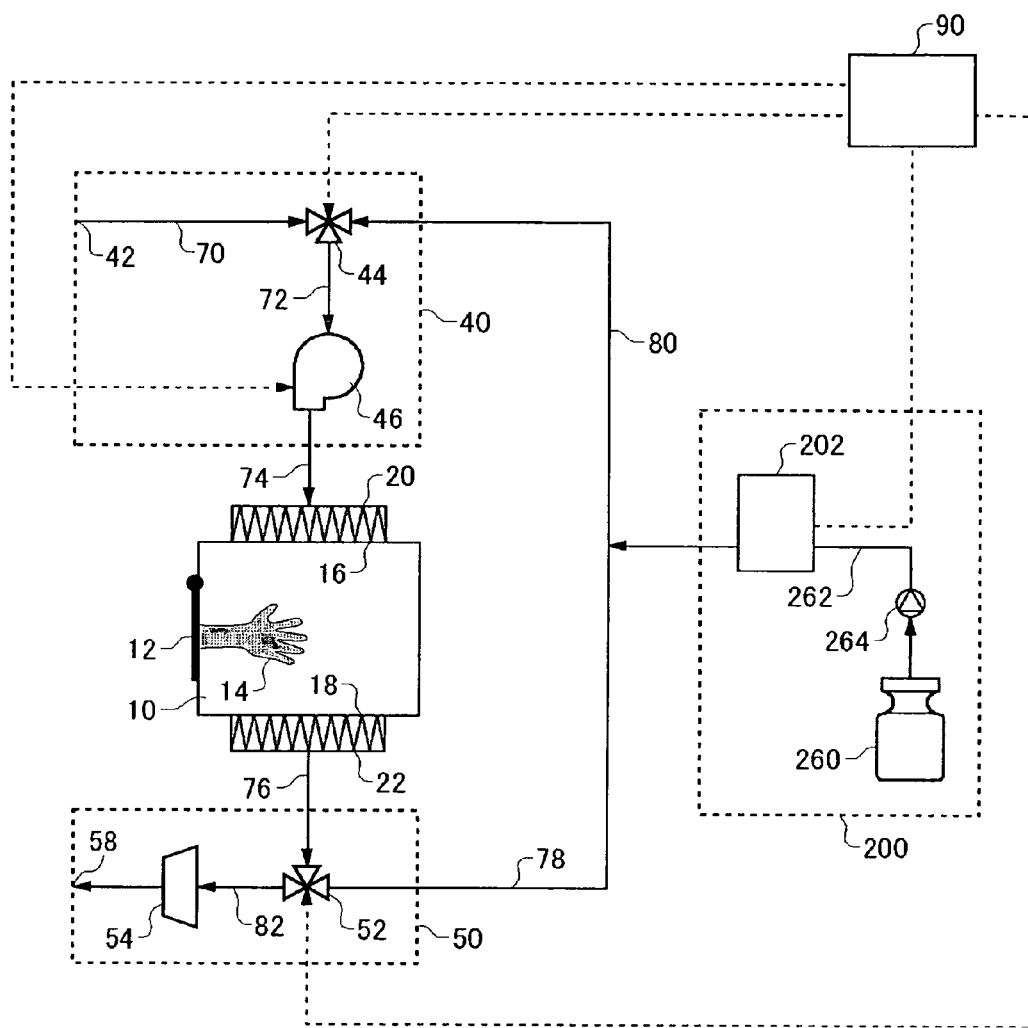
FIG. 1 is a schematic diagram showing a structure of an isolator according to a first embodiment of the present invention.

The invention will now be described by reference to the preferred embodiments. This does not intend to limit the scope of the present invention, but to exemplify the invention.

Hereinbelow, the embodiments will be described with reference to the accompanying drawings. Note that in each Figure the same reference numerals are given to the same components and the description thereof is omitted as appropriate.

First Embodiment

FIG. 1 is a schematic diagram showing a structure of an isolator 100 according to a first embodiment of the present invention. As shown in FIG. 1, the isolator 100 of the first embodiment includes a workroom 10, in which a work involving biologically-derived materials such as cell extraction or cell culture is performed, a gas supply unit 40 for supplying a gas, a gas discharge unit 50 for discharging the gas in the workroom 10, a sterilizing material supply apparatus 200 for supplying a sterilizing material to the workroom 10, and a control unit 90 for controlling these components. Note that biologically-derived materials meant here are materials such as living organisms themselves including cells, substances constituting the living organisms, and substances produced by the living organisms.

The gas supply unit 40 is provided with an air inlet 42, a three-way valve 44, and a fan 46. Air is taken in from the outside via the air inlet 42. The three-way valve 44 is connected downstream of gas flow of the air inlet 42 via a path 70 and downstream of gas flow of a sterilizing gas generator 202 via a path 80. Also, the three-way valve 44 is connected upstream of gas flow of the fan 46 via a path 72. The three-way valve 44 is capable of exclusively switching the gas flow path toward either the path 72 from the path 70 or the path 72 from the path 80. The air taken in via the air inlet 42 or the gas, including the sterilizing material, sent out via the path 80 is taken in by the fan 46 via the three-way valve 44.

The fan 46 blows out the gas taken in via the path 72 from a direction where three-way valve 44 is disposed, toward a direction where the workroom 10 is disposed, via a path 74. The fan 46 can perform on-off control by the control unit 90. Note that the fan 46 can continuously adjust the air volume displacement.

The workroom 10 is provided with a front door 12 which is openable and closable. A work glove 14 to be used in operations in the workroom 10 is installed in a predetermined position of the front door 12. A worker can insert his/her hand into the work glove 14 through a not-shown opening provided in the front door 12 and perform work in the workroom 10 via the work glove 14. Air sent out from the fan 46 enters the workroom 10 from a gas supply port 16, and is discharged from a gas discharge port 18. The gas supply port 16 is provided with a HEPA (High-Efficiency Particulate Air) filter 20, and the gas supply port 18 is provided with a HEPA filter 22. Such an arrangement as described above ensures that the workroom 10 is maintained sterile. Air flowing out of the workroom 10 is sent out to the gas discharge unit 50 by way of he gas discharge port 18, the HEPA filter 22 and a path 76.

The gas discharge unit 50 is comprised of a three-way valve 52, a sterilizing material reduction unit 54 and a discharge port 58 arranged in this order along the gas flow.

The three-way valve 52 is connected downstream of gas flow of the workroom 10 via the path 76 and upstream of gas flow of the sterilizing material reduction unit 54 via the path 82. Also, the three-way valve 52 is connected upstream of gas flow of the sterilizing material supply apparatus 200 (described later) via a path 78. The three-way valve 52 is capable of exclusively switching the gas flow path toward either the path 82 from the path 76 or the path 78 from the path 76. The gas taken in via the path 76 is sent out toward the path 82 or path 78.

The sterilizing material reduction unit 54 reduces the concentration level of the sterilizing material contained in the gas sent out via the three-way valve 52. The sterilizing material reduction unit 54 may include a metallic catalyst, such as platinum, and may include an activated carbon or the like.

The sterilizing material supply apparatus 200 for supplying the sterilizing material to the workroom 10 is disposed exterior to the workroom 10. The sterilizing material supply apparatus 200 can create a sterile environment in the workroom 10 and the paths by supplying the sterilizing material into the workroom 10 and circulating it within the isolator 100. Note that the sterile environment meant here is an environment substantially free of dust and germs such that it allows no entry of substances other than the materials used in the work done in the workroom. In the present embodiment, the sterilizing material, or sterilant (sterilizing agent), is hydrogen peroxide.

As shown in FIG. 1, the sterilizing material supply apparatus 200 is connected downstream of gas flow of the three-way valve 52 and the path 78 and upstream of gas flow of the path 80 and the three-way valve 44. The sterilizing material supply apparatus 200 includes a sterilizing material cartridge 260, a pump 264, and a sterilizing gas generator 202. The sterilizing material cartridges 260 stores the water solution of hydrogen peroxide as the sterilizing material. The pump 264 pumps up the hydrogen peroxide solution stored in the sterilizing material cartridge 260 and sends it out to the sterilizing gas generator 202. The sterilizing gas generator 202 vaporizes the hydrogen peroxide solution supplied and generates a hydrogen peroxide gas. The thus generated hydrogen peroxide gas is sent out to the path 80.

Figure 2A:
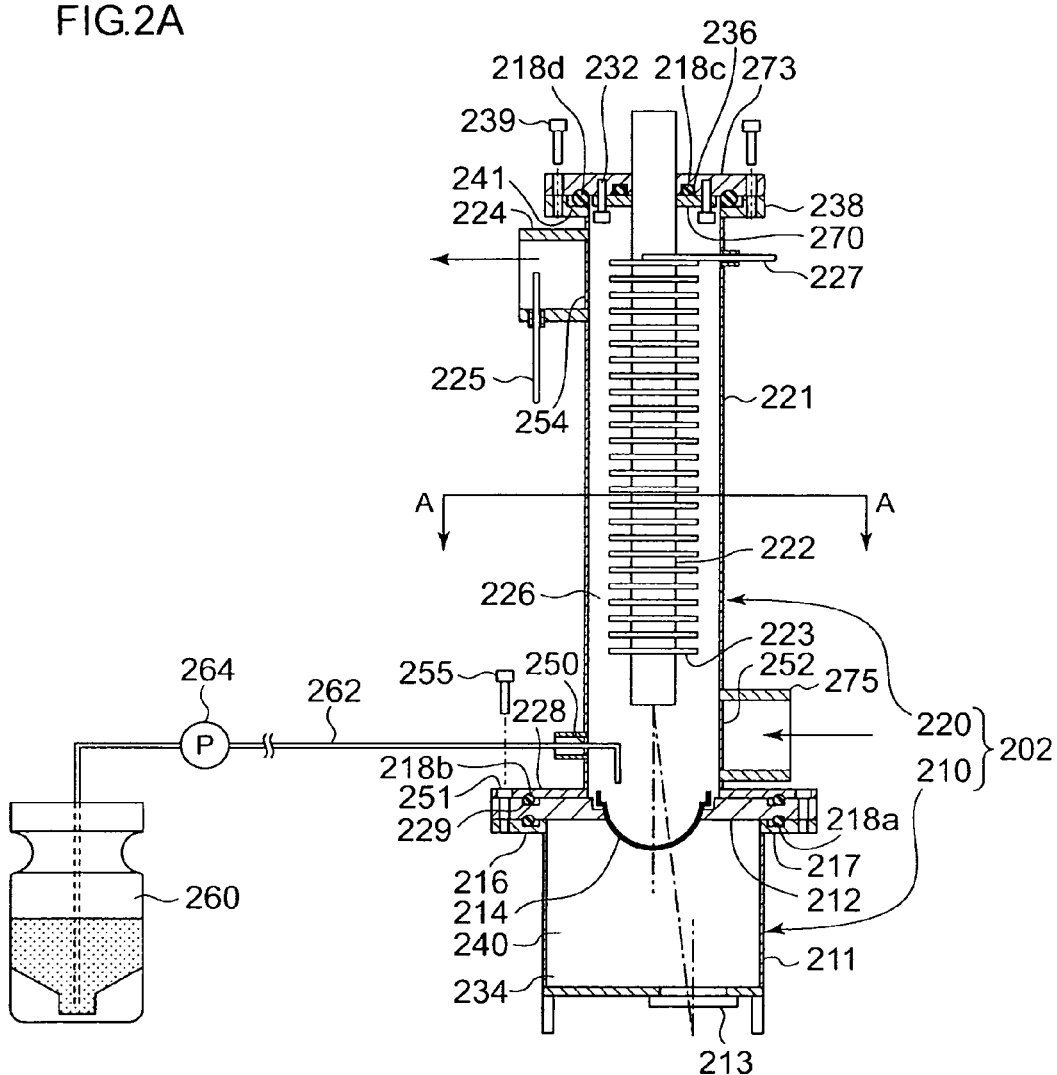
FIG. 2A is a schematic diagram showing a structure of a sterilizing material supply apparatus included in an isolator according to a first embodiment of the present invention.
Figure 2B:
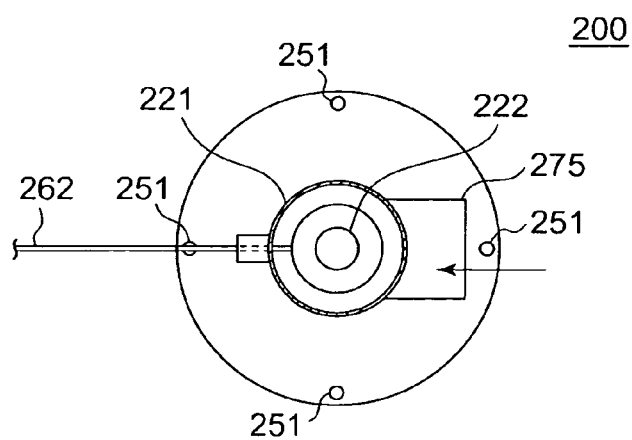
FIG. 2B is a cross-sectional view taken along the line A-A of FIG. 2A.

A concrete structure of the sterilizing material supply apparatus 200 will now be described in detail with reference to FIG. 2A and FIG. 2B. FIG. 2A is a schematic diagram showing a structure of the sterilizing material supply apparatus 200 according to a first embodiment of the present invention. FIG. 2B is a cross-sectional view taken along the line A-A of FIG. 2A.

As shown in FIG. 2A, the sterilizing material supply unit 200 includes the sterilizing gas generator 202 which is comprised of a mist generation unit (atomizing unit) 210 and a vaporizing unit 220.

The mist generation unit 210 includes a holding member 211, a partition member 212, an ultrasonic vibrator 213, and a cup 214 serving as a receptacle for holding the hydrogen peroxide solution which is a raw material for sterilizing agent.

The holding member 211 is a propagation fluid holding unit that constitutes the mist generation unit 210. The ultrasonic vibrator 213 is disposed on the bottom of the holding member 211. The ultrasonic vibrator 213 is a device that converts electrical energy into ultrasonic vibration. In the present embodiment, the ultrasonic vibrator 213 is not placed in the center of the bottom of the holding member 211 but in a position dislocated closer to an opening 252 to be described later.

A flange 216 is formed around the top periphery of the holding member 211. The top surface of the flange 216 is provided with a groove 217 into which an O-ring 218a is fitted.

The partition member 212 is disposed on top of the flange 216. The partition member 212 is a doughnut-shaped member with an opening formed in the middle thereof. The outside diameter of the partition member 212 is the same as that of the flange 216. The top surface of the partition member 212 is provided with a groove 229 into which an O-ring 218b is fitted.

The cup 214 is attached to the opening provided in the partition member 212, and the bottom of the cup 214 projects toward the ultrasonic vibrator 213. The cup 214 is made of a polyester resin, such as PET, having a thickness of about 0.2 mm or of a metal sheet, such as stainless steel, having a thickness of about 0.05 mm, for instance.

A space 234 enclosed by the holding member 211, the partition member 212, and the cup 214 is filled with an ultrasonic propagation liquid 240 which is used to propagate the ultrasonic vibration generated by the ultrasonic vibrator 213. Note that the liquid recommendable as the ultrasonic propagation liquid is water or similar liquid with low viscosity.

In the mist generation unit 210 configured as described above, the hydrogen peroxide solution supplied to the cup 214 is turned into a mist by the ultrasonic vibration propagated through the ultrasonic propagation liquid 240, and the hydrogen peroxide turned into mist is sent into the vaporizing unit 220. In this process, droplets of hydrogen peroxide adhering to the inside of the vaporizing unit 220 without becoming mist will drop to the cup 214 by the force of gravity and will be turned into mist again.

It should be appreciated here that the wavefront direction of the ultrasonic vibration generated by the ultrasonic vibrator 213, namely the direction normal to the center of the vibration surface of the ultrasonic vibrator 213, is tilted toward the direction where the lowest part of the cup is located or the direction where the lowest part of the heater 222 (described later) is located. The direction normal to the center of the vibration surface thereof is preferably tilting about 7 degrees, for example, relative to the vertical direction (i.e., the vertical direction of the mist generation unit 210). In such an arrangement, the water column by the hydrogen peroxide solution stored by the cup 214 rises up at a tilt, so that a stable mist generation of the hydrogen peroxide solution can be accomplished.

The vaporizing unit 220, which is disposed above the atomizing unit 210, is comprised mainly of a heating pipe 221, a heater 222, a piping 224, and thermometers 225 and 227.

The heating pipe 221 is mounted on top of the holding member 211 in such a manner that its axial direction is vertical. To be more specific, the heating pipe 221 has a flange 228 formed around the lower end thereof. The outside diameter of the flange 228 is the same as those of the partition member 212 and the flange 216.

The flange 216, the partition member 212 and the flange 228 are provided with screw holes 251 in predetermined positions. The atomizing unit 210 and the vaporizing unit 220 are assembled by screwing screws 255 into the screw holes 251 with the O-rings 218a and 218b fitted in the grooves 217 and 229, respectively. Airtightness between the flange 216 and the partition member 212 is enhanced by the O-ring 218a. Also, airtightness between the flange 228 and the partition member 212 is enhanced by the O-ring 218b.

The heating pipe 221 has an opening 250 and an opening 252 in the lower part thereof. In the present embodiment, the opening 250 and the opening 252 are located in positions opposite to each other. Led through the opening 250 is the piping 262 which supplies the hydrogen peroxide solution stored in the sterilizing material cartridge 260 to the cup 214. Provided midway along the piping 262 is a pump 264 (e.g., Peristaltic pump) which is used to pump up the hydrogen peroxide solution stored in the sterilizing material cartridge 260.

On the other hand, connected to the opening 252 is a piping 275 into which air (carrier gas) sent out from an air supply fan (not shown) flows, which constitutes a carrier gas supply port. The path 78 may be connected to the opening 252. By implementing this arrangement, the sterilizing material gas generator 202 comprised of the mist generation unit 210 and the vaporizing unit 220 functions as a part of the circulating path that goes through the workroom 10, so that the hydrogen peroxide solution can be supplied to the circulating path as necessary.

Inside the heating pipe 221, a flow path 226 is formed where hydrogen peroxide and air flow from bottom upward.

In the present embodiment, the heating pipe 221 is disposed directly above the cup 214. Therefore, even when the hydrogen peroxide mist recombines into droplets within the heating pipe 221, they will drop down to the cup 214 by the force of gravity. The hydrogen peroxide having returned to the cup 214 will again be turned into a mist by the ultrasonic vibration and sent to the heating pipe 221. Thus, the hydrogen peroxide liquefied in the heating pipe 221 is returned to the cup 214 and turned into mist again by a simple structure, thereby accomplishing a complete gasification of hydrogen peroxide solution in the cup 214.

The heater 222 is disposed inside the heating pipe 221 along its axis. The heater 222 is regulated at a temperature of about 180° C. through the ON/OFF control by the control unit 300. The temperature of the heater 222 is detected by the thermometer 227, and the detected temperature is transmitted to the control unit 300. When the temperature of the heater 222 exceeds about 220° C., the control unit 300 cuts off power supply to the heater 222. Note that the heater 222 is preferably provided with a plurality of fins 223. Such an arrangement will promote gasification of hydrogen peroxide by increasing the contact area between the heater 222 and the hydrogen peroxide flowing through the flow path 226.

A flange 270 for fixation is provided in the upper part of the heater 222. A lid member 273 has a groove 236 formed along the periphery of the heater 222, and an O-ring 218c is fitted in this groove 236. Also, the lid member 273 is provided with an opening through which the upper portion of the heater 222 is inserted. The heater 222 is fastened to the lid member 273 by means of screws 232, and the O-ring 218c enhances airtightness between the flange 270 and the lid member 273.

The heating pipe 221 is provided with a flange 238 at the top portion of the heating pipe 221. The flange 238 has a groove 241 formed in its surface facing the lid member 273, and an O-ring 218d is fitted in this groove 241. The flange 238 is fastened to the lid member 273 by means of screws 239. In this manner, the lid member 273 is mounted on the heating pipe 221 with the O-ring 218d enhancing airtightness, and at the same time the state of the heater 222 inserted in the heating pipe 221 is maintained.

The heating pipe 221 has an opening 254 in a side face of the upper part of the heating pipe 221, to which one end of the piping 224 is connected. This opening 254 constitutes a hydrogen peroxide supply port for supplying not only the carrier gas but also the hydrogen peroxide to the exterior. Provided on the piping 224 is the thermometer 225 which is used to measure the internal temperature of the piping 224. The internal temperature of the piping 224 measured by the thermometer 225 is transmitted to the control unit 300. Connected to the other end of the piping 224 are the downstream end of the first sterilizing material supply path 78 and the upstream end of the second sterilizing material supply path 80.

Figure 3:
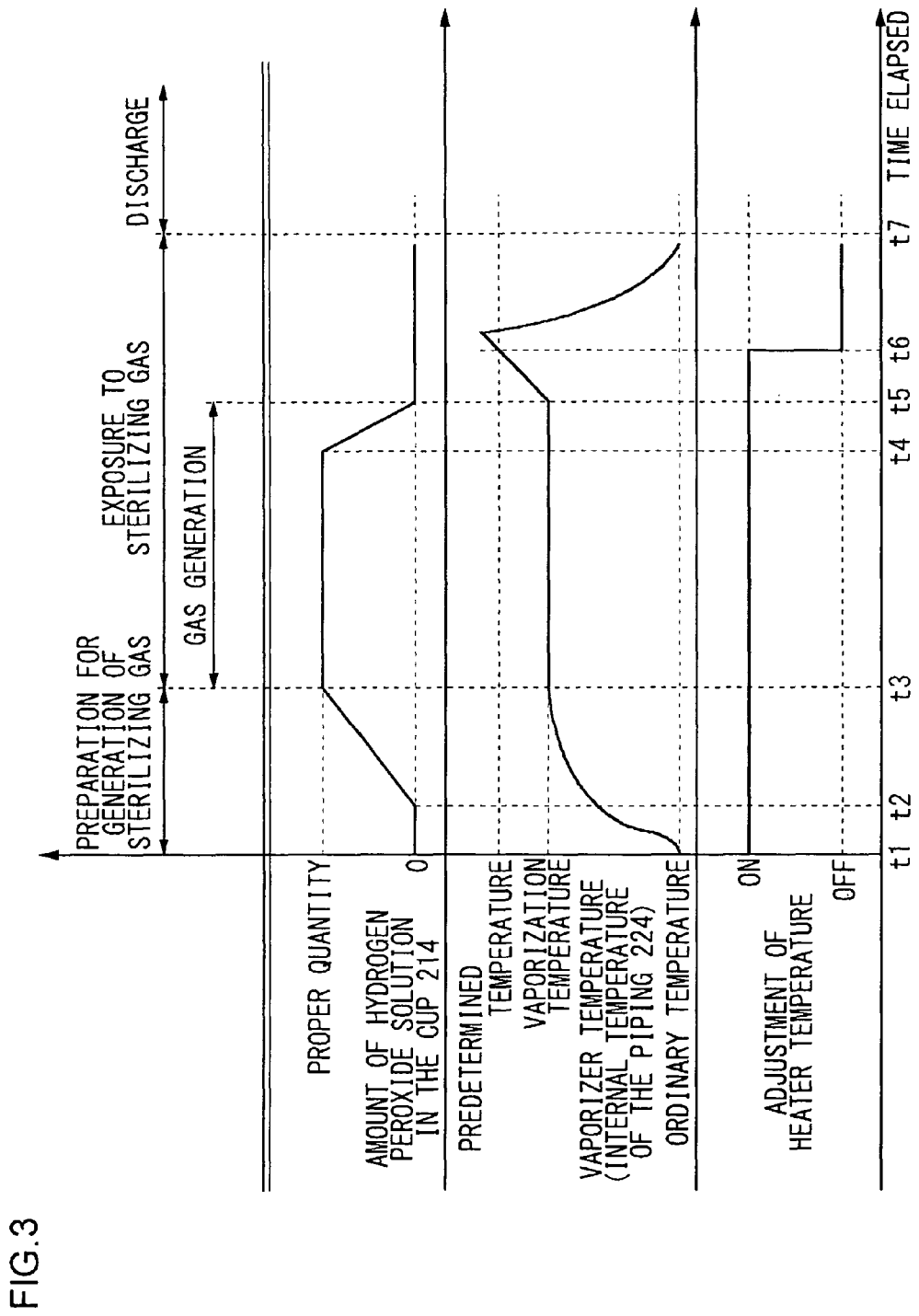
FIG. 3 is a timing chart for explaining a method of generating a sterilizing gas in a sterilizing material supply apparatus included in an isolator according to a first embodiment of the present invention.

A description is now given of an operation of generating a sterilizing gas in the sterilizing material supply apparatus 200 structured as above, with reference to the timing charts of FIG. 3. Note that the generation of sterilizing gas by the sterilizing material supply apparatus 200 is controlled by the control unit 90.

At time t1, the heater 222 is first switched on and the heating of the heater 222 starts. At the same time, the hydrogen peroxide solution stored in the sterilizing material cartridge 260 is pumped up by driving the pump 264, and the hydrogen peroxide solution is delivered toward the cup 214.

As the heater 222 is switched on, the internal temperature of the piping 224 starts to rise from an ordinary temperature. As, at time t2, the hydrogen peroxide solution reaches the cup 214 after having passed through the piping 262, the hydrogen peroxide solution starts to accumulate at the bottom of the cup 214 and therefore the amount of hydrogen peroxide solution in the cup 214 starts to rise.

As the internal temperature of the piping 224 reaches the vaporization temperature of hydrogen peroxide at time t3, the ultrasonic vibrator 213 starts to be driven and the ultrasonic vibration propagates to the cup 214 through the ultrasonic propagation fluid 240. The supply of air starts and therefore the air is sent into the cup 214 from the outside. As a result, the hydrogen peroxide is turned into a mist in the cup 214, and the hydrogen peroxide which has been turned into mist is supplied to the heating pipe 221 by the air sent from the air-supply fan. The hydrogen peroxide in the form of mist supplied to the heating pipe 221 is heated by the heater 222 so as to be completely gaseous. The gaseous hydrogen peroxide is supplied to the path 80 by way of the piping 224.

In a mist generation apparatus using the ultrasonic vibrator, the mist generation efficiency varies according to the distance between the surface of the ultrasonic vibrator and the liquid level up to which the mist is generated. Thus it is known in the art that an appropriate distance must be maintained. Accordingly, it is desirable that the flow rate at which the hydrogen peroxide solution is delivered to the cup 214 by the pump 264 be adjusted in such a manner as to supplement the hydrogen peroxide solution in the cup 214 consumed along with the progress of mist generation and gasification. As a result, at time t3 and thereafter, the hydrogen peroxide solution in the cup 214 can be efficiency turned into mist. The total amount of hydrogen peroxide solution delivered to the cup 214 is predetermined, so that the drive of the pump 264 is stopped after a predetermined period of time, which is set according to the capacity of the pump 264, has elapsed.

As the drive of the pump 264 has stopped at time t3 or later, the supply of the hydrogen peroxide solution to the cup 214 is stopped at time t4. After time t4, the amount of hydrogen peroxide solution in the cup 214 drops gradually and the remaining amount thereof becomes zero at time t5.

After time t5, the amount of hydrogen peroxide in the form of mist sent from the mist generation unit 210 and the vaporizing unit 220 drops gradually. Thus the heat quantity released by the vaporization of hydrogen peroxide in the heating pipe 221 drops gradually. As a result, the internal temperature of the piping 224 rises further above the vaporization temperature of hydrogen peroxide. In other words, the rise of the internal temperature of the piping 224 is a phenomenon indicating that the remaining amount of hydrogen peroxide in the cup 214 becomes zero. Thus, detecting this phenomenon allows one to estimate whether the remaining amount of hydrogen peroxide is zero or not. When the internal temperature of the piping 224 measured by the thermometer 225 reaches a predetermined temperature at time t6, the drive of the ultrasonic vibrator 213 is stopped and the heater 222 is switched off, thereby stopping the heating by the heater 222. Note that the predetermined temperature corresponds to the internal temperature of the piping 224 in a state where the gasification of hydrogen peroxide in the heating pipe 221 has completed and only the air inside the heating pipe 221 starts to move. That is, the phenomenon that the internal temperature of the piping 224 reaches the predetermined temperature indicates that the remaining amount of hydrogen peroxide solution in the cup 214 becomes zero and no hydrogen peroxide solution to be gasified exists in the sterilizing material supply apparatus 200.

After time t6, the internal temperature of the piping 224 continues to rise and then drops gradually. At time t7, the internal temperature thereof returns to an ordinary temperature.

The time period from time t1 to time t3 corresponds to a time duration required for the sterilizing gas to be generated. From time t3 to time t4, the mist generation unit 210 generates the mist from the hydrogen peroxide. From time t1 to time t7, the sterilizing gas is exposed to paths including the workroom 10 (i.e., a pretreatment process and a sterilization process to be discussed later). After time t7, the sterilizing gas is discharged from the paths including the workroom 10 (i.e., a replacement process to be discussed later).

A description is now given of the control unit 90 by referring back to FIG. 1. As described above, the control unit 90 controls the delivery of sterilizing gas by the sterilizing material supply apparatus 200. Also, the control unit 90 switches the gas flow path by controlling the opening and closing of valves in the three-way valves 44 and 52.

More specifically, the control unit 90 controls the opening and closing of valves of the three-way valve 44 and thereby controls the exclusive switching of the gas flow path to either the path 72 from the path 70 or the path 72 from the path 80. Also, the control unit 90 controls the opening and closing of valves of the three-way valve 52 and thereby controls the exclusive switching of the gas flow path to either the path 82 from the path 76 or the path 78 from the path 76.

(The Switching of Gas Flow Path)

The gas paths in the isolator 100 are switched as follows in two difference ways when the control unit 90 controls the opening and closing of the three-way valves 44 and 52. That is, when the hydrogen peroxide gas is circulated in the isolator 100, the three-way valve 44 is set such that only a passage connecting from the path 80 to the path 72 is opened and a passage leading from the path 70 to the path 72 is closed. Also, the three-way valve 52 is set such that only a passage connecting from the path 76 to the path 78 is opened and a passage connecting from the path 76 to path 82 is closed.

When, on the other hand, the replacement of air in the workroom is to be done, the three-way valve 44 is set such that only the passage leading from the path 70 to the path 72 is opened and the passage leading from the path 80 to path 72 is closed. Also, the three-way valve 52 is set such that only a passage leading from the path 76 to the path 82 is opened and the passage leading from the path 76 to path 78 is closed. With this configuration described as above, a sequence of paths is formed as followed. Air enters from the air inlet 42 and flows into the workroom 10 after passing through the three-way valve 44, the path 72, the fan 46, the path 74, the HEPA filter 20 and the gas supply port 16. Then the air is discharged from the discharge port 58 after passing through the gas discharge port 18, the HEPA filter 22, the path 76, the three-way valve 52, the path 82 and the sterilizing material reduction unit 54.

(Sterilization Treatment)

In the isolator 100, after the end of one operation (previous work) in the workroom 10, a sterilization treatment of the workroom 10 and the paths used in the previous work is performed before the start of the next operation. The sterilization treatment includes a pretreatment process, a sterilization process, and a replacement process.

In the pretreatment process, the hydrogen peroxide gas is supplied into the workroom 10 from the sterilizing material supply apparatus 200, so that the concentration of hydrogen peroxide gas is maintained at a level or above, which is required for the sterilization of the workroom 10. After the concentration of hydrogen peroxide gas in the workroom 10 in the pretreatment process has reached a prescribed level or above, the sterilization process starts.

In the process of sterilization, a circulation path is formed such that the hydrogen peroxide gas is sent to the workroom 10 from the sterilizing material supply apparatus 200 and is returned again to the sterilizing material supply apparatus 200. In so doing, the three-way valve 44 is switched to the open state only in the passage connecting from the path 80 to the path 72, and is switched to the closed state in the passage connecting from the path 70 to the path 72. On the other hand, the three-way valve 52 is switched to the open state only in the passage connecting from the path 76 to the path 78, and is switched to the closed state in the passage connecting from the path 76 to the path 82. Thus, a gas flow path is formed in the isolator 100 such that the gas flows from the three-way valve 44 into the workroom 10 and then returns to the three-way valve 44 via the three-way valve 52. And the hydrogen peroxide gas introduced into the workroom 10 can be circulated within the isolator 100 by controlling the operation of the fan 46. The HEPA filters 20 and 22, the paths 74 and 76 and the like can be sterilized, as necessary, by controlling the flow path and the fan in this manner.

In the replacement process, air taken in via the air inlet 42 is supplied into the workroom 10 and the gas inside the workroom 10 is pushed out, so that the gas inside the workroom 10 is replaced. More specifically, in the replacement process, the three-way valve 44 is switched to the open state only in a passage connecting from the air inlet 42 to the workroom 10, and the three-way valve 52 is switched to the open state only in a passage connecting from the workroom 10 to the discharge port 58. The control unit 90 turns the fan 46 on. This forms a gas flow path in the isolator 100 such that the air taken in from the air inlet 42 passes through the HEPA filter 20 from the path 70, reaches the workroom 10, then passes through the HEPA filter 22 from the workroom 10, and is discharged from the discharge port 58. As a result, the gas inside the workroom 10 is replaced by air and therefore the hydrogen peroxide gas in the workroom 10 is removed from the workroom 10.

At the same time, the hydrogen peroxide gas pushed out of the workroom 10 is subjected to a reduction treatment by the sterilizing material reduction unit 54, so that the outflow of hydrogen peroxide gas from the discharge port 58 to the exterior is reduced. In the replacement process, the hydrogen peroxide gas staying on within a region other than the workroom 10 in the isolator 100, for example, within the gas supply unit 40 and the hydrogen peroxide adsorbed by the HEPA filters 20 and 22 in the flow paths used in the previous work are also removed.

By employing the isolator 100 as described above, the following advantageous effects can be achieved.

Since the hydrogen peroxide which has been converted into mists by the mist generation unit 20 is gasified by the vaporizing unit 20, the gasification of hydrogen peroxide in the vaporizing unit 220 is conducted promptly. Consequently, the quantity of heat used in the vaporizing unit can be reduced as compared with the conventional practice. Thus, the time duration required for the gasification of hydrogen peroxide can be shortened and consequently the process of sterilization as a whole can be shortened. As a result, the work efficiency in the isolator 100 can be improved.

After a predetermined amount of hydrogen peroxide solution has been supplied into the cup 214 by the pump 264, whether the internal temperature of the piping 224 has been reached to a predetermined temperature or not is determined. This can indicate the fact that the remaining amount of hydrogen peroxide solution in the cup 214 is zero. As a result, the temperature of the heater 222 can be completely regulated and the consumption of energy in the isolator 100 can be minimized. Also, the process can be promptly switched from the sterilization process to the replacement process immediately after the remaining amount of hydrogen peroxide solution in the cup 214 becomes empty. Hence, wasting time can be significantly reduced and the time spent in the process of sterilization as a whole can be shortened.

(Sterilizing Material Supply Apparatus According to a First Modification)

Figure 4A:
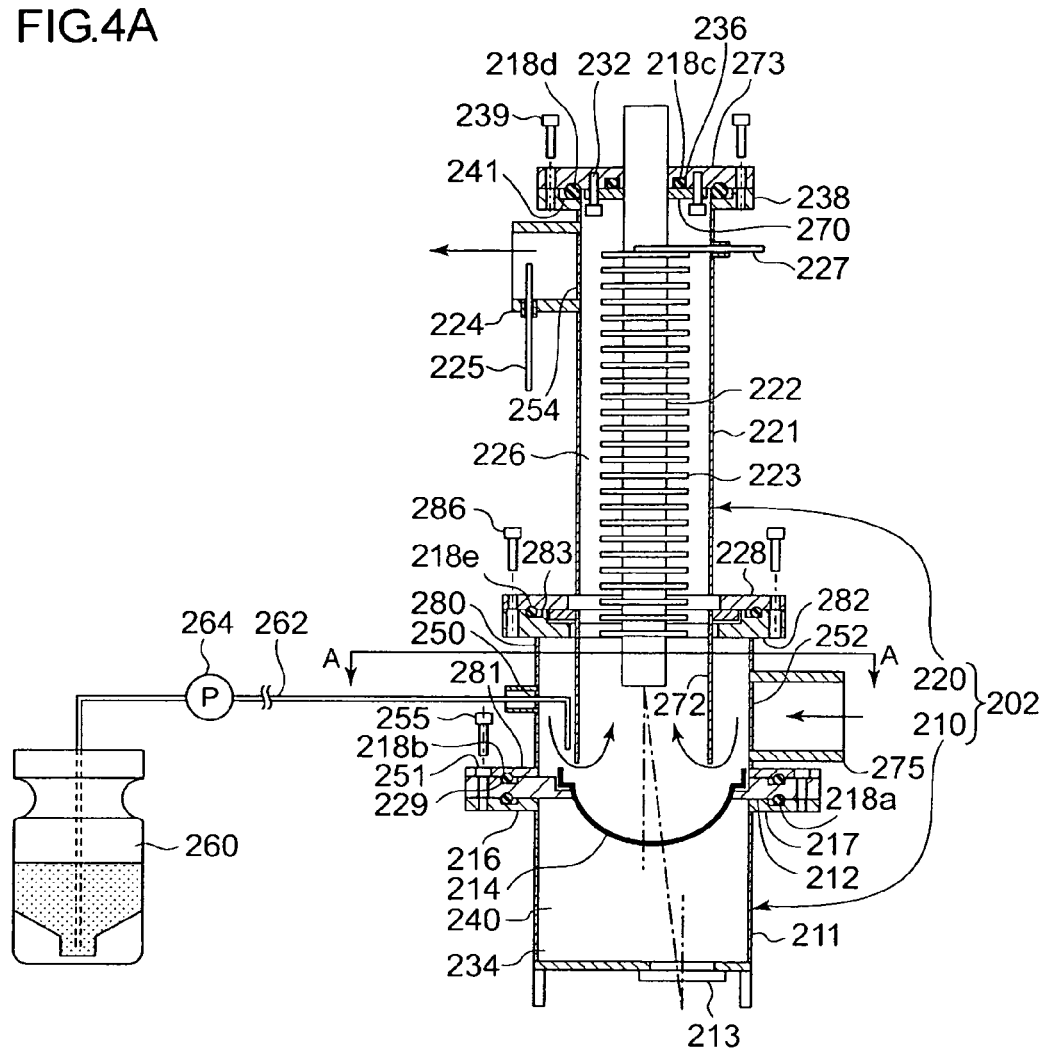
FIG. 4A is a schematic diagram showing a sterilizing supply apparatus according to a first modification.
Figure 4B:
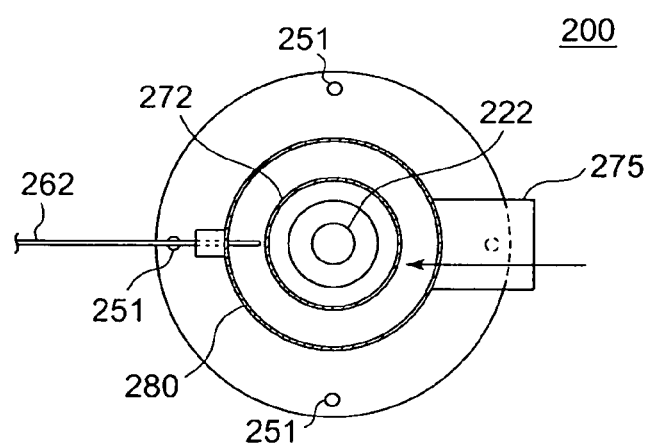
FIG. 4B is a cross-sectional view taken along the line A-A of FIG. 4A.

A description is now given of the sterilizing material apparatus 200 of a first modification, with reference to FIG. 4A and FIG. 4B. FIG. 4A is a schematic diagram showing the sterilizing supply apparatus 200 according to the first modification. FIG. 4B is a cross-sectional view taken along the line A-A of FIG. 4A.

The basic structure of the modifications to the sterilizing material apparatus 200 is similar to that described in the first embodiment. Thus the same structural components as those of the first embodiment is omitted as appropriate and a description is hereinbelow given centering around the difference therefrom.

In the sterilizing material supply apparatus 200 according to the first modification, the heating pipe 221 and the holding member 211 are assembled together by way of a connecting member 280 (connector). The diameter of the connecting member 280 is identical to that of the holding member 211 and is larger than that of the heating pipe 221.

A flange 281 is formed around the lower periphery of the connecting member 280. The outside diameter of the flange 281 is the same as that of the partition member 212 and the flange 216.

The flange 216, the partition member 212 and the flange 218 are provided with screw holes 251 in predetermined positions. The mist generation unit 210 and the connecting member 280 are assembled by screwing screws 255 into the screw holes 251 with the O-rings 218a and 218b fitted in the grooves 217 and 229, respectively. Airtightness between the flange 216 and the partition member 212 is enhanced by the O-ring 218a. Also, airtightness between the flange 281 and the partition member 212 is enhanced by the O-ring 218b.

In this modification, the opening 250 and the opening 252 are located in positions opposite to each other in the lower side surface of the connecting member 280.

A flange 282 is formed around the top periphery of the connecting member 280. The top surface of the flange 282 is provided with a groove 283, into which an O-ring 218a is fitted, and a notch 285, into which an end of an internal pipe 272 inserted into the connection member 280 is fitted. The diameter of the internal pipe 272 is the same as that of the heating pipe 221, and the internal pipe 272 serves as an extending member of the heating pipe 221.

The flange 282 is fastened around the lower periphery of the heating pipe 221 by means of the flange 228 and a screw 286. In this case, the O-ring 218e enhances airtightness between the flange 282 and the flange 228.

In the sterilizing material supply apparatus 200 according to the first modification as configured above, the inside of the connecting member 280 is of a double structure due to the internal pipe 272. Thus, in a space between the internal pipe 272 and the connecting member 280, the hydrogen peroxide solution is converted into droplets downwardly facing the cup 214 from the piping 262. In a space between the internal pipe 272 and the connecting member 280, a carrier gas supplied through the piping 275 flows downward to the cup 214. It is desirable that the lowest end of the internal pipe 272 is located below the lowest end (the lowest point of the inside diameter) of an opening (the carrier gas supply port) through which the carrier gas enters.

On the other hand, inside the internal pipe 272, the hydrogen peroxide solution atomized by the mist generation unit 210 flows upwardly together with the carrier gas. Then the thus atomized hydrogen peroxide solution flows into the heating pipe 221 by way of the internal pipe 272.

In this manner, the inside of the connecting member 280 is of a double structure by the use of the internal pipe 272. Thus, the flow of the carrier gas is downward in the space between the internal pipe 272 and the connecting member 280, whereas it is upward inside the internal pipe 272 because it changes its direction to the opposite on the outer circumference of the cup 214. As a result, the water column can be stably formed on the surface of the hydrogen peroxide solution stored by the cup 214. Also, since the lowest end of the internal pipe 272 is located below the lowest end of the opening 252 through which the carrier gas enters, the occurrence of a disturbance in the flow of the aforementioned carrier gas can be minimized.

(Sterilizing Material Supply Apparatus According to a Second Modification)

Figure 5A:
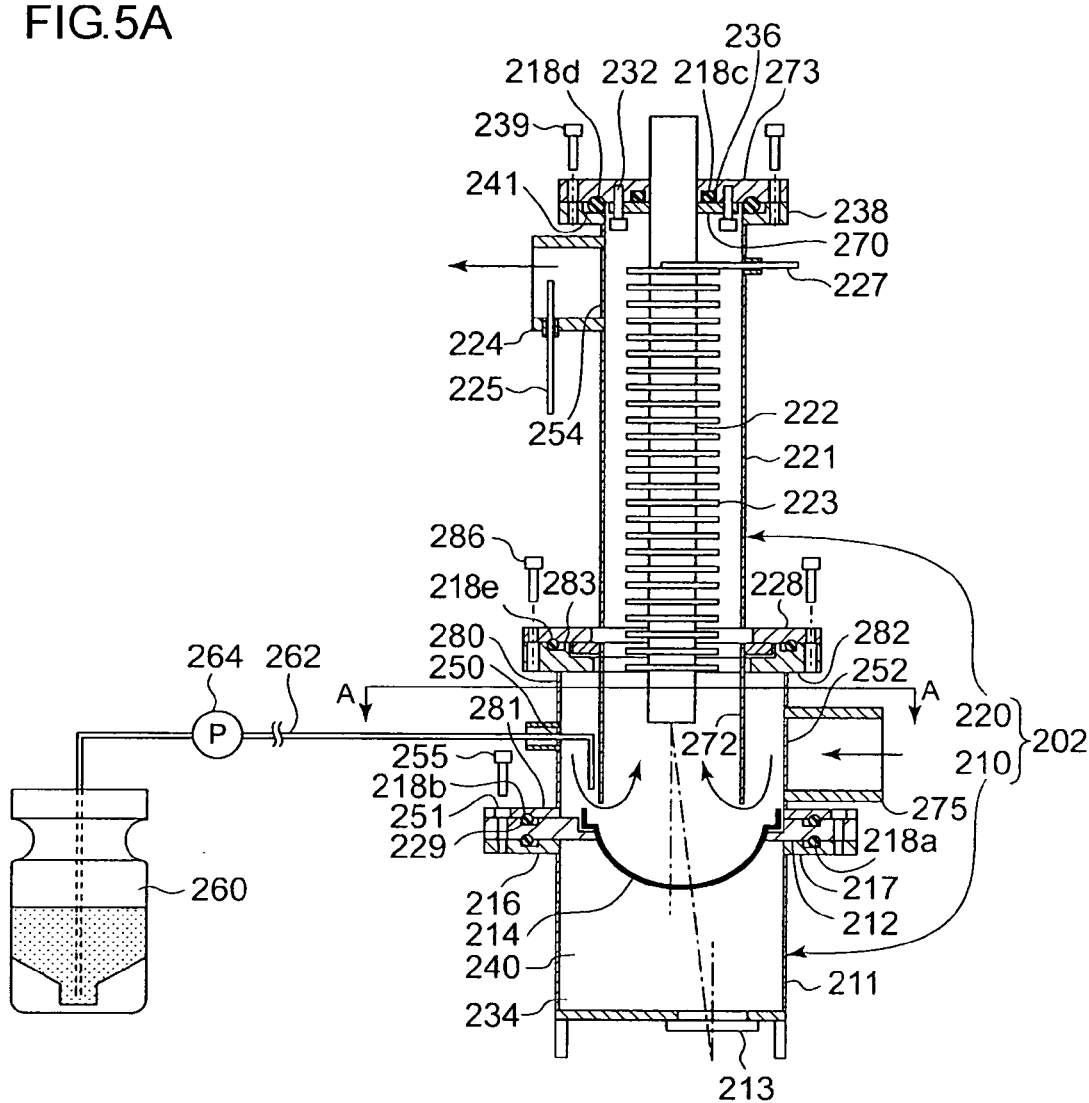
FIG. 5A is a schematic diagram showing a sterilizing supply apparatus according to a second modification.
Figure 5B:
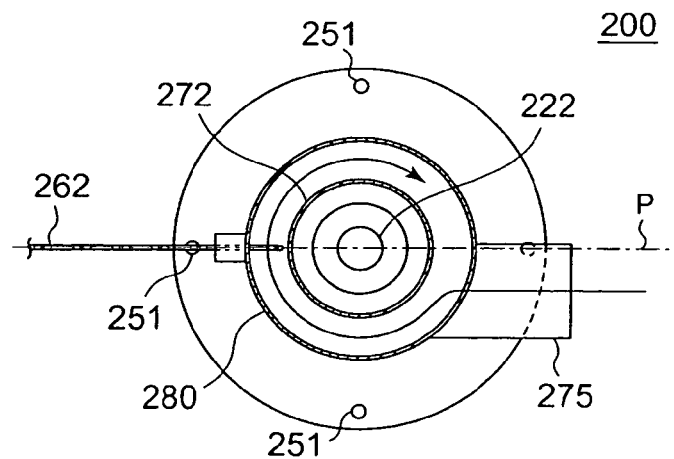
FIG. 5B is a cross-sectional view taken along the line A-A of FIG. 5A.

A description is now given of the sterilizing material apparatus 200 of a second modification, with reference to FIG. 5A and FIG. 5B. FIG. 5A is a schematic diagram showing the sterilizing supply apparatus 200 according to the second modification. FIG. 5B is a cross-sectional view taken along the line A-A of FIG. 5A.

The structure of the sterilizing material supply apparatus 200 according to the second modification is basically the same as that of the first modification and therefore a description is hereinbelow given of differences therefrom.

In the sterilizing material supply apparatus 200 according to the second modification, the center of the piping 275 is displaced from a line P passing through the center of the heater 222 (or the center of the connecting member 280), as shown in FIG. 5B. By implementing this arrangement, the flow of the carrier gas is downward in the space between the internal pipe 272 and the connecting member 280, and the flow direction thereof is clockwise as shown in the cross-sectional view of FIG. 5B. Thus, when the carrier gas folds back on the outer circumference of the cup 214, the flow thereof becomes an upward flow of a spiral nature. As a result, the water column can be more stably formed on the surface of the hydrogen peroxide solution stored by the cup 214.

While the preferred embodiments of the present invention and their modifications have been described using specific terms, such description is for illustrative purposes only, and it is to be understood that changes and variations may further be made without departing from the spirit or scope of the appended claims.

What is claimed is:

1. A sterilizing material supply apparatus comprising:
a mist generation unit including:
   a propagation fluid holding unit for holding a fluid through which ultrasonic vibration generated by an ultrasonic vibrator attached to a bottom of said holding unit propagates; and
   a receptacle for holding a hydrogen peroxide solution which is a raw material for sterilizing material,
      the receptacle being attached onto the propagation fluid holding unit in such a manner as to cover an upper opening of the propagation fluid holding unit, and
      a bottom of the receptacle projecting toward the ultrasonic vibrator; and
a vaporizing unit configured to heat and vaporize the hydrogen peroxide solution atomized by said mist generation unit wherein said vaporizing unit is installed upright above said mist generation unit, wherein a lower opening of said vaporizing unit communicates with the receptacle,
said vaporizing unit including:
   a carrier gas supply port into which a carrier gas carrying the hydrogen peroxide solution atomized thereby flows through a lower side face of said vaporizing unit;
   a heating pipe, disposed on top of said mist generating unit, having a hydrogen peroxide supply port for supplying hydrogen peroxide, together with the carrier gas, to the exterior; and
   a heater disposed inside the heating pipe,
wherein the hydrogen peroxide solution atomized by said mist generation unit is fed to said vaporizing unit using the carrier gas, and a hydrogen peroxide gas vaporized by said vaporizing unit, together with the carrier gas is supplied to the exterior.

2. A sterilizing material supply apparatus according to claim 1, further comprising a connection member configured to connect said mist generation unit to said vaporizing unit, said connection member having the carrier gas supply port on a side face thereof
   wherein a diameter of said connection member is greater than that of the heating pipe, and
   in said connection member a lower end of the heating pipe extends further downward from a lower end of the carrier gas supply port.

3. A sterilizing material supply apparatus according to claim 1, wherein a direction normal to a center of vibrator surface of the ultrasonic vibrator faces the receptacle at a tilt relative to a vertical direction.

4. A sterilizing material supply apparatus according to claim 2, wherein a direction normal to a center of vibrator surface of the ultrasonic vibrator faces the receptacle at a tilt relative to a vertical direction.

5. An isolator having a workroom in which a work involving biologically-derived materials is performed, the isolator comprising:
   a mist generation unit including:
      a propagation fluid holding unit for holding a fluid through which ultrasonic vibration generated by an ultrasonic vibrator attached to a bottom of the holding unit propagates; and
      a receptacle for holding a hydrogen peroxide solution which is a raw material for sterilizing material,
         the receptacle being attached to the propagation fluid holding unit in such a manner as to cover an upper opening of the propagation fluid holding unit, and
         a bottom of the receptacle projecting toward the ultrasonic vibrator; and
   a vaporizing unit configured to heat and vaporize the hydrogen peroxide solution atomized by said mist generation unit wherein said vaporizing unit is installed upright above said mist generation unit, wherein a lower opening of said vaporizing unit communicates with the receptacle,
the vaporizing unit including:
      a carrier gas supply port into which a carrier gas carrying the hydrogen peroxide solution atomized thereby flows through a lower side face of said vaporizing unit;
      a heating pipe, disposed on top of said mist generating unit, having a hydrogen peroxide supply port for supplying hydrogen peroxide, together with the carrier gas, to the exterior; and
      a heater disposed inside the heating pipe,
wherein the hydrogen peroxide solution atomized by the mist generation unit is fed to the vaporizing unit using the carrier gas, and a hydrogen peroxide gas vaporized by said vaporizing unit, together with the carrier gas is supplied to the exterior.

\* \* \* \* \*